(12) United States Patent
Petschke et al.

(10) Patent No.: US 9,345,445 B2
(45) Date of Patent: May 24, 2016

(54) REGISTRATION OF 4th-GENERATION DETECTORS RELATIVE TO 3rd-GENERATION CT SYSTEM COORDINATES USING 4th-GENERATION DETECTOR SHADOW PATTERN

(71) Applicants: Kabushiki Kaisha Toshiba, Minato-ku (JP); Toshiba Medical Systems Corporation, Otawara-shi (JP)

(72) Inventors: Adam Petschke, Lake Bluff, IL (US); Yuexing Zhang, Naperville, IL (US); Xiaolan Wang, Buffalo Grove, IL (US)

(73) Assignees: KABUSHIKI KAISHA TOSHIBA, Minato-ku (JP); TOSHIBA MEDICAL SYSTEMS CORPORATION, Otawara-shi (JP)

( * ) Notice: Subject to any disclaimer, the term of this patent is extended or adjusted under 35 U.S.C. 154(b) by 194 days.

(21) Appl. No.: 14/197,976

(22) Filed: Mar. 5, 2014

(65) Prior Publication Data

US 2015/0250443 A1   Sep. 10, 2015

(51) Int. Cl.
| | |
|---|---|
| *A61B 6/00* | (2006.01) |
| *A61B 6/03* | (2006.01) |
| *G06K 9/32* | (2006.01) |
| *G06K 9/62* | (2006.01) |
| *G06T 7/00* | (2006.01) |

(52) U.S. Cl.
CPC ................ *A61B 6/584* (2013.01); *A61B 6/032* (2013.01); *A61B 6/4241* (2013.01); *G06K 9/32* (2013.01); *G06K 9/6202* (2013.01); *G06K 9/6212* (2013.01); *G06T 7/003* (2013.01); *G06T 7/0012* (2013.01); *G06T 7/0014* (2013.01); *G06T 7/0026* (2013.01); *G06T 7/0034* (2013.01)

(58) Field of Classification Search
IPC ................... A61B 6/00,6/02, 6/03, 6/032, 6/42, A61B 6/4208, 6/4241, 6/4266, 6/4275, 6/52, A61B 6/5229, 6/5235, 6/5258, 6/582, 6/583, A61B 6/584, 6/585; G05B 1/00, 1/01, 1/03; G06F 3/14, 3/1415, 11/00, 11/07, 11/0703, G06F 11/0706, 11/0733, 17/30244, 17/30247, G06F 19/30, 19/32, 19/321; G06K 9/20, G06K 9/32, 9/3208, 9/3216, 9/3233, 9/60, G06K 9/62, 9/6202, 9/6203, 9/6201, 9/6212, G06K 9/6215, 9/78, 9/80; G06T 7/00, 7/0002, G06T 7/0012, 7/0014, 7/0022, 7/0024, 7/0026, G06T 7/0028, 7/003, 7/0034, 7/60, 7/602, G06T 2207/10072, 2207/10076, 2207/10081, G06T 2207/10084, 2207/20212, 2207/20221
See application file for complete search history.

(56) References Cited

U.S. PATENT DOCUMENTS

2007/0100225 A1* 5/2007 Maschke ................ A61B 6/032
600/407

* cited by examiner

*Primary Examiner* — Anastasia Midkiff
(74) *Attorney, Agent, or Firm* — Oblon, McClelland, Maier & Neustadt, L.L.P

(57) ABSTRACT

A method is provided for determining, in a fourth-generation computed tomography (CT) scanner, a positional offset of a center of a ring of fixed energy-discriminating detectors with respect to an iso-center of a third-generation X-ray source/detector system. The method includes obtaining a plurality of offset images, each offset image being obtained from a scan executed with the ring of fixed energy-discriminating detectors positioned in a known offset location with respect to the iso-center; performing a current scan executed with the ring positioned in an unknown offset location with respect to the iso-center, to obtain a current image; calculating, for each offset image, a corresponding error value between the offset image and the current image; and determining the positional offset of the center of the ring to be an offset location corresponding to an offset image having the smallest error value.

13 Claims, 7 Drawing Sheets

REGISTRATION OF 4$^{th}$-GENERATION DETECTORS RELATIVE TO 3$^{rd}$-GENERATION CT SYSTEM COORDINATES USING 4$^{th}$-GENERATION DETECTOR SHADOW PATTERN

FIELD

Embodiments disclosed herein generally relate to computed tomography (CT) imaging. In particular, embodiments disclosed herein relate to a system and an associated method to register 4$^{th}$-generation detectors relative to 3$^{rd}$-generation CT system coordinates using the shadow pattern of the 4$^{th}$-generation detector.

BACKGROUND

X-ray computed tomography (CT) imaging, in its simplest expression, is an X-ray beam traversing an object and a detector relating the overall attenuation per ray. The attenuation is derived from a comparison of the same ray with and without the presence of the object. From this conceptual definition, several steps are required to properly construct an image. For instance, the finite size of the X-ray generator, the nature and shape of the filter blocking the very low energy X-ray from the generator, the details of the geometry and characteristics of the detector, and the capacity of the acquisition system are all elements that affect how the actual reconstruction is performed.

For a combined 3$^{rd}$-generation and 4$^{th}$-generation CT scanner, the system matrix requires knowledge of the offset of the 4$^{th}$-generation sparse photon-counting detectors relative to the 3$^{rd}$-generation CT system coordinates. If the offset between the 3$^{rd}$-generation isocenter and the 4$^{th}$-generation detectors is not know precisely, the system matrix will be incorrect, which will cause artifacts in the reconstructed image. Moreover, the offset could change over time due to temperature-induced expansion of materials and gantry rotation.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1:
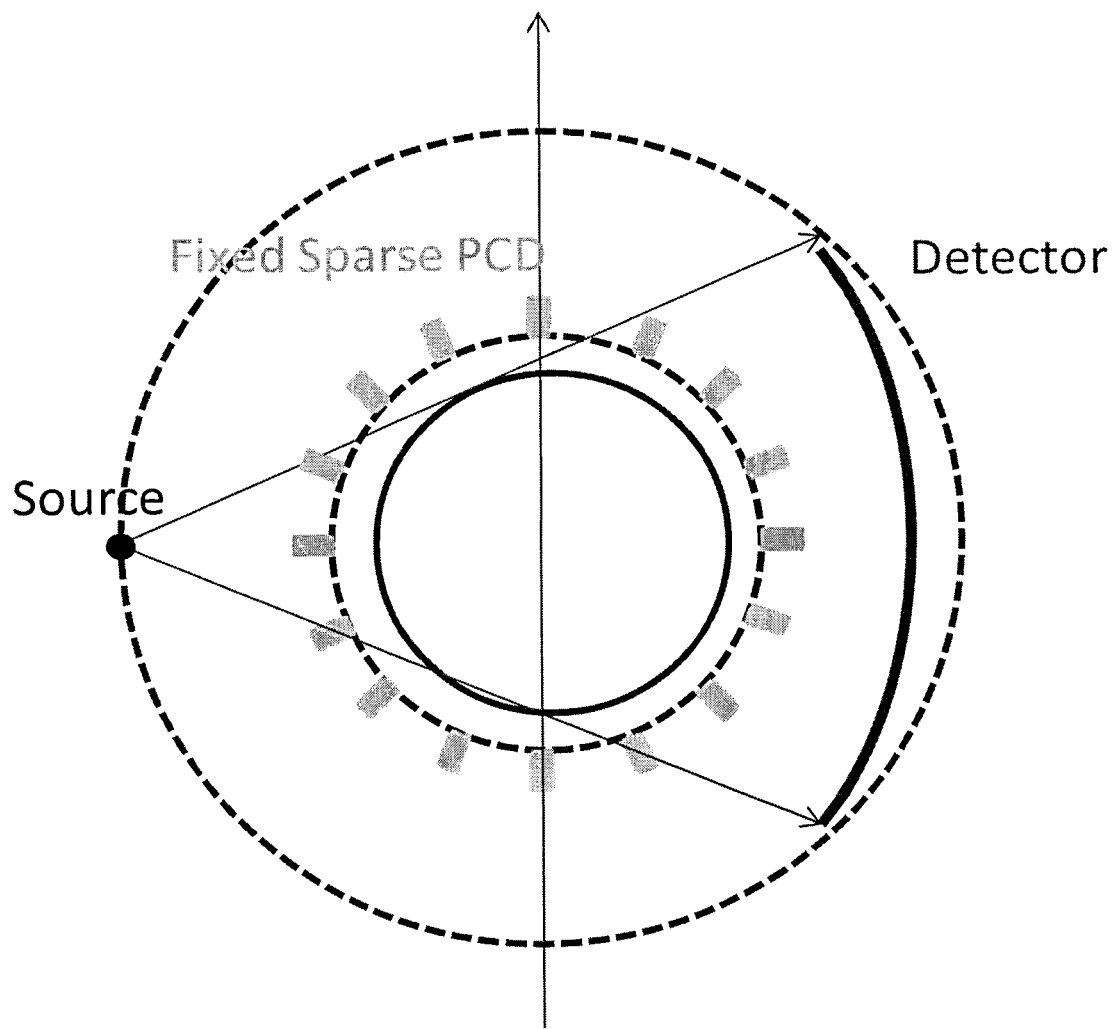
FIG. 1 illustrates a CT scanner apparatus including a sparse fixed photon-counting detector ring, a rotating X-ray source, and third-generation detectors.

In one embodiment there is provided a method for determining, for a fourth-generation computed tomography (CT) scanner, a positional offset of a center of a ring of fixed energy-discriminating detectors with respect to an iso-center of a third-generation X-ray source/detector system, the method comprising: (1) obtaining a plurality of offset images, each offset image being obtained from a scan executed with the ring of fixed energy-discriminating detectors positioned in a known offset location with respect to the iso-center of the third-generation X-ray source/detector system; (2) performing a current scan executed with the ring of fixed energy-discriminating detectors positioned in an unknown offset location with respect to the iso-center of the third-generation X-ray source/detector system, to obtain a current image; (3) calculating, for each offset image, a corresponding error value between the offset image and the current image to obtain a plurality of error values; (4) determining a smallest error value of the plurality of error values; and (5) determining the positional offset of the center of the ring of fixed energy-discriminating detectors to be an offset location corresponding to an offset image, of the plurality of offset images, having the determined smallest error value.

In another embodiment the obtaining step comprises obtaining the offset images from a database of offset images, each offset image being generated by an air scan or a scan of a known phantom.

In another embodiment, the calculating step comprises calculating, for each offset image, a mean-squared error between pixels in the current image and pixels in the offset image.

In another embodiment, the obtaining step comprises obtaining the plurality of offset images so that the plurality of offset images include images generated when the ring of fixed energy-discriminating detectors is positioned at various known offset positions around the iso-center of the third-generation X-ray source/detector system. For example, the known offset positions are arranged in a two-dimensional grid centered at the iso-center of the third-generation X-ray source/detector system.

In another embodiment there is provided a method for determining, for a fourth-generation computed tomography (CT) scanner, a positional offset of a center of a ring of fixed energy-discriminating detectors with respect to an iso-center of a third-generation X-ray source/detector system, the method comprising: (1) obtaining a plurality of offset images, each offset image being obtained from a scan executed with the ring of fixed energy-discriminating detectors positioned in a known offset location with respect to the iso-center of the third-generation X-ray source/detector system; (2) performing a current scan executed with the ring of fixed energy-discriminating detectors positioned in an unknown offset location with respect to the iso-center of the third-generation X-ray source/detector system, to obtain a current image; (3) calculating, for each offset image, a corresponding correlation value between the offset image and the current image to obtain a plurality of error values; (4) determining a largest correlation value of the plurality of correlation values; and (5) determining the positional offset of the center of the ring of fixed energy-discriminating detectors to be an offset location corresponding to an offset image, of the plurality of offset images, having the determined largest correlation value.

In another embodiment, there is provided an apparatus for determining, in a fourth-generation computed tomography (CT) scanner, a positional offset of a center of a ring of fixed energy-discriminating detectors with respect to an iso-center of a third-generation X-ray source/detector system, the apparatus comprising: a processing circuit configured to execute a program that causes the processing circuit to (1) obtain a plurality of offset images, each offset image being obtained from a scan executed with the ring of fixed energy-discriminating detectors positioned in a known offset location with respect to the iso-center of the third-generation X-ray source/detector system; (2) perform a current scan executed with the ring of fixed energy-discriminating detectors positioned in an unknown offset location with respect to the iso-center of the third-generation X-ray source/detector system, to obtain a current image; (3) calculate, for each offset image, a corresponding error value between the offset image and the current image to obtain a plurality of error values; (4) determine a smallest error value of the plurality of error values; and (5) determine the positional offset of the center of the ring of fixed energy-discriminating detectors to be an offset location corresponding to an offset image, of the plurality of offset images, having the determined smallest error value.

The apparatus can further include a memory that stores the plurality offset images, each offset image being stored in association with a corresponding offset location of the offset image.

Turning now to the drawings, FIG. 1 illustrates a combine third/fourth generation system having stationary, sparsely distributed fourth generation detectors, along with a rotating third generation source/detector system.

Figure 4:
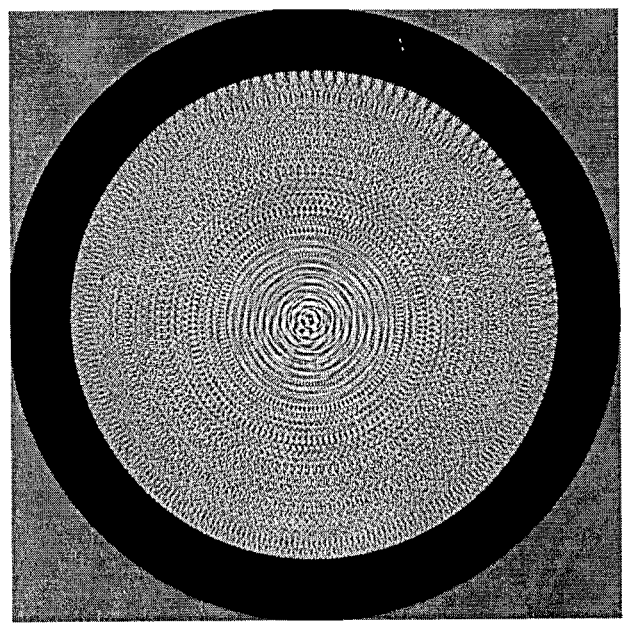
Figure 5:
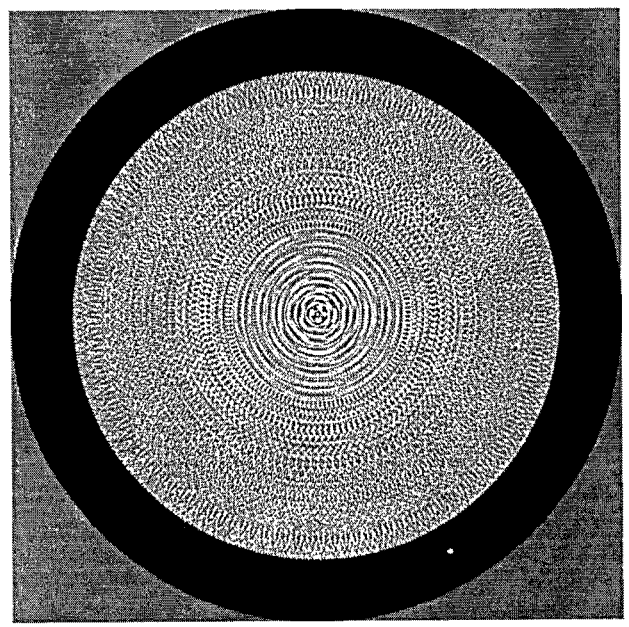

As can be seen from FIGS. 4 and 5, shadows from the $4^{th}$-generation detectors create artifacts in the resulting $3^{rd}$-generation image. The present inventors recognized that the artifacts will have a well-defined pattern and that the artifact pattern changes based on the position of $4^{th}$-generation detectors relative to the $3^{rd}$-generation isocenter. Accordingly, in the present embodiments, the artifact pattern is used to register the center of the $4^{th}$-generation detectors to the $3^{rd}$-generation isocenter in the x-y plane.

Figure 3:
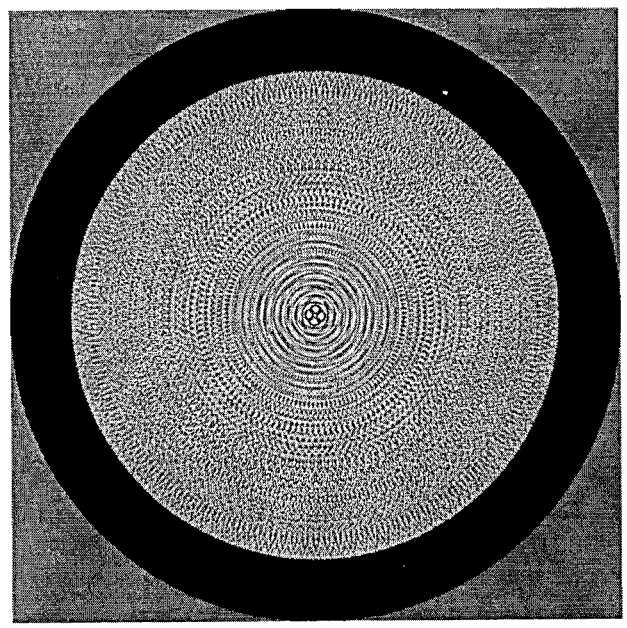
FIGS. 3-5 illustrate CT images obtained with various offsets for the center of the 4$^{th}$-generation detector ring.

For example, FIG. 3 illustrates a $3^{rd}$-generation image in which the inner, sparse ring is centered at the iso-center. In contrast, in FIG. 4, the inner ring is offset and is centered at x=−2 mm, y=−4 mm. Further, in FIG. 5, the inner ring is offset and is centered at x=1 mm, y=0.5 mm.

Figure 2A:
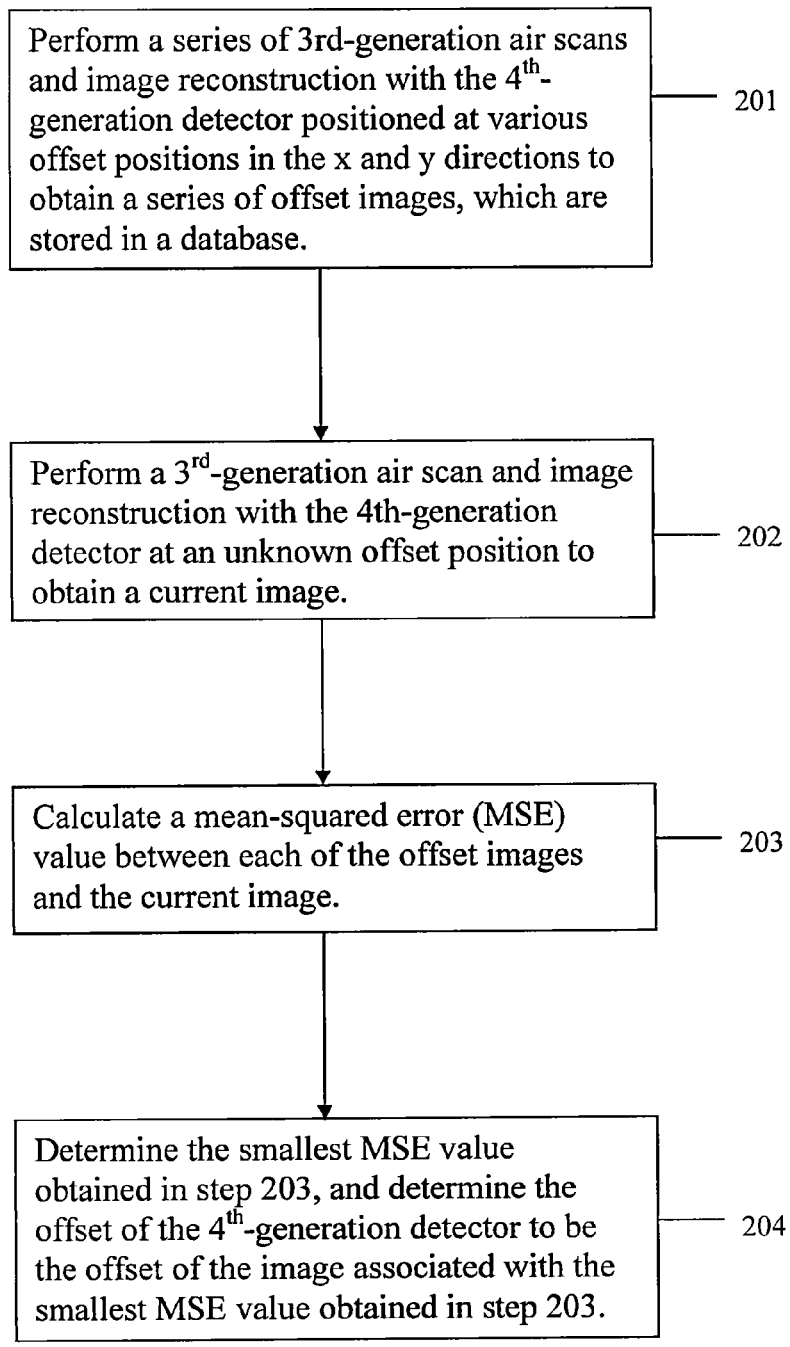
FIGS. 2A and 2B illustrate offset determination methods of the present embodiments.

In one embodiment, as shown in FIG. 2A, the offset of the $4^{th}$-generation sparse ring from the $3^{rd}$-generation iso-center is calculated using the following method.

In step 201, $3^{rd}$-generation images are reconstructed with the $4^{th}$-generation detector located in various known offset positions, e.g., with an air scan or a phantom scan. For example, ten x-direction offsets and ten y-direction offsets are used to generate 100 images. Other numbers of x and y offsets can be used. The obtained images are obtained once (or periodically) and stored in a database in a memory for later use.

In step 202, a current $3^{rd}$-generation image is obtained for a scanner (having an unknown offset) at some time after the images in step 201 are obtained.

In step 203, the mean-squared error (MSE) between the pixel values of the current image and the pixel values of each of the offset images is calculated, e.g., as $$MSE^{(j)} = \frac{1}{N}\sum_{i=1}^{N}(x_i - y_i^{(j)})^2$$

where N is the number of pixels, $x_i$ is the $i^{th}$ pixel of the image, and $y_i^{(j)}$ is the $i^{th}$ pixel of the $j^{th}$ offset image. Using absolute value, the formula is $$\frac{1}{N}\sum_{i=1}^{N}|x_i - y_i^{(j)}|.$$

In step 204, the offset of the current image is determined to be the same as the offset of the image having the smallest MSE calculated in step 203. Additionally, bilinear interpolation can be used for greater accuracy in finding the offset.

Figure 2B:
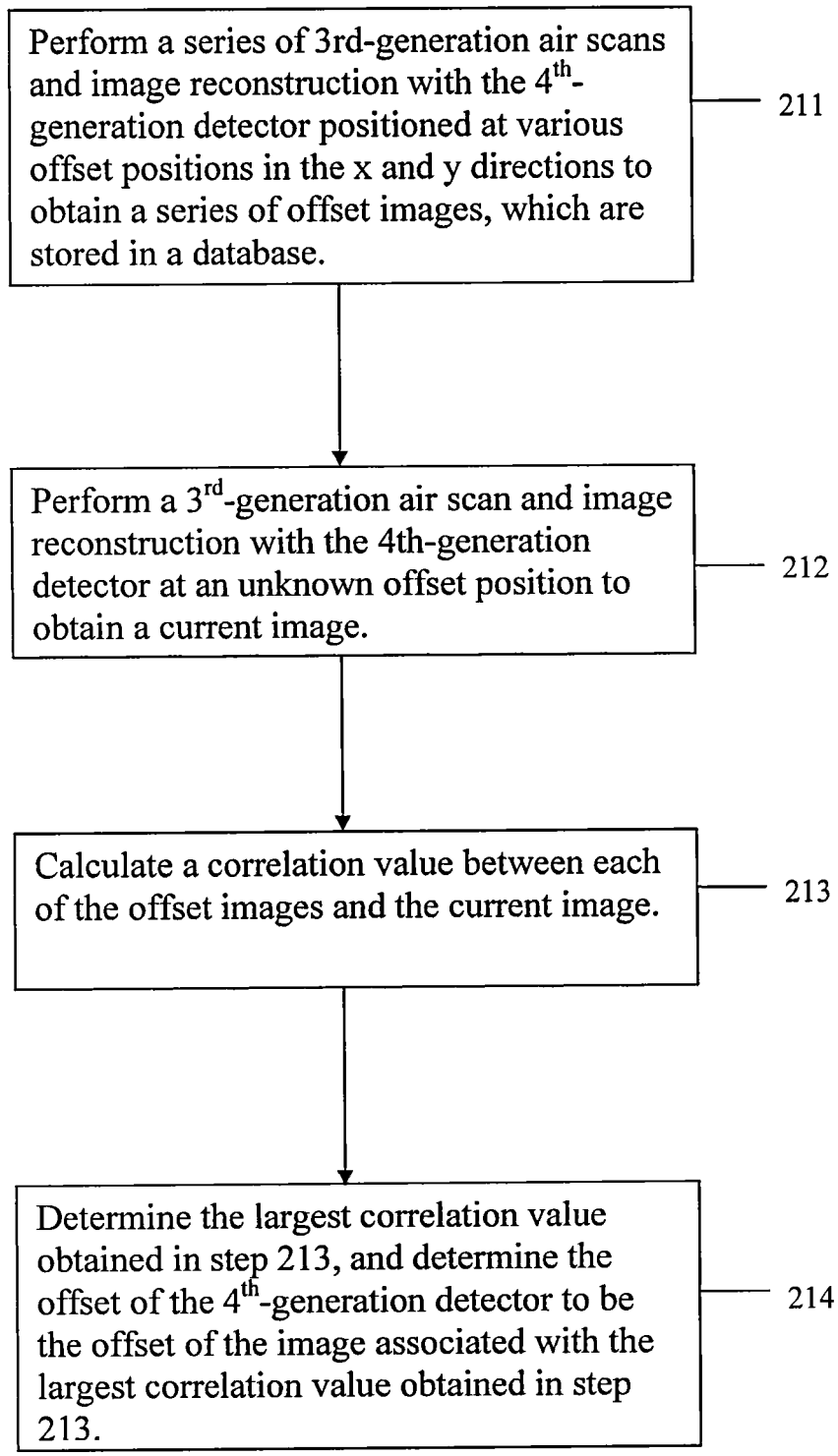

In another embodiment, as shown in FIG. 2B, the offset of the $4^{th}$-generation sparse ring from the $3^{rd}$-generation iso-center is calculated using the following method.

In step 211, $3^{rd}$-generation images are reconstructed with the $4^{th}$-generation detector located in various known offset positions, e.g., with an air scan or a phantom scan. For example, ten x-direction offsets and ten y-direction offsets are used to generate 100 images. Other numbers of x and y offsets can be used. The obtained images are obtained once (or periodically) and stored in a database in a memory for later use.

In step 212, a current $3^{rd}$-generation image is obtained for a scanner (having an unknown offset) at some time after the images in step 211 are obtained.

In step 213, a correlation value between the current image and all of the offset images is calculated. For example, the cross-correlation can be computed as:

$$(x*y)[j] = \sum_{i=1}^{N} x_i y_i^{(j)}$$

where $x_i$, $y_i$, and N are defined above.

In step 214, the offset of the current image is determined to be the same as the offset of the image having the maximum correlation calculated in step 213. Additionally, bilinear interpolation can be used for greater accuracy in finding the offset.

Figure 6:
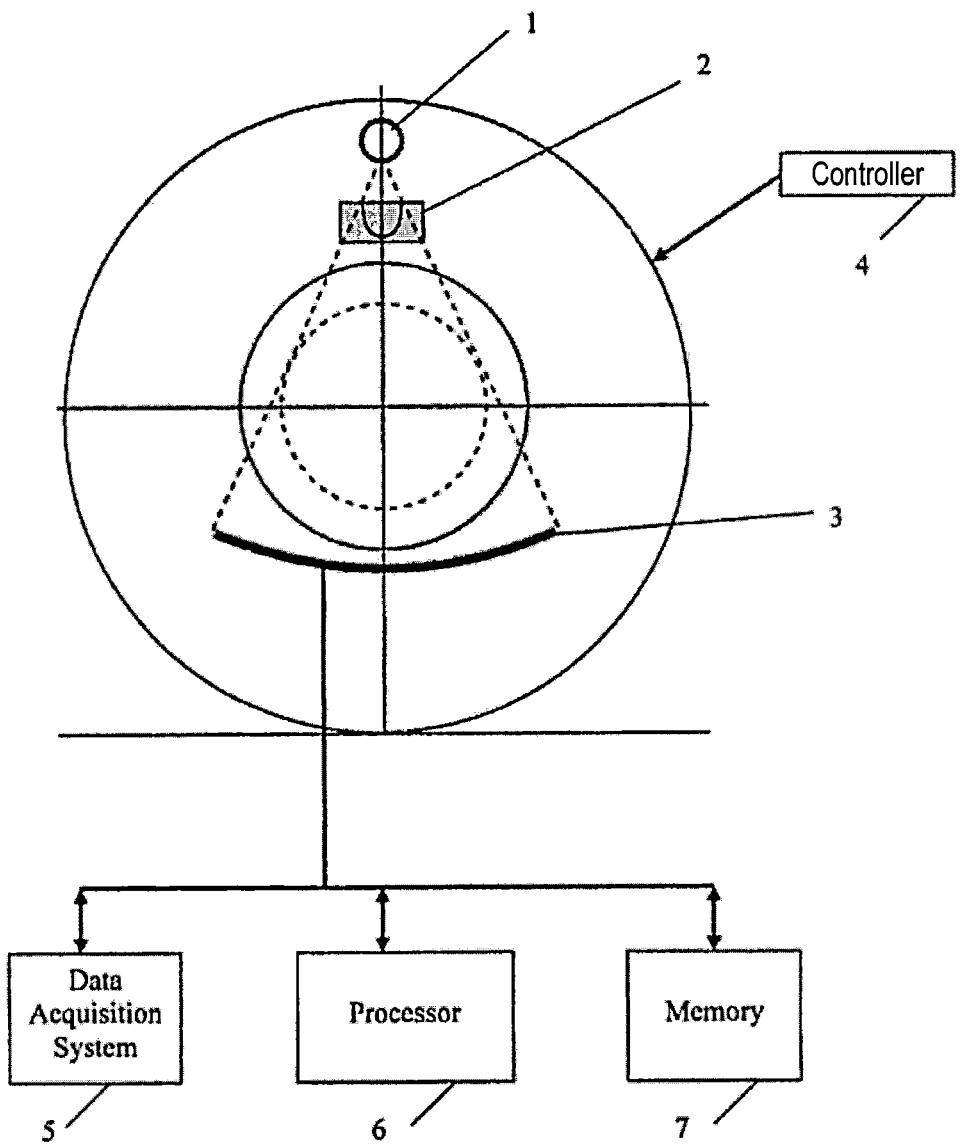
FIG. 6 illustrates a CT scanner system according to the present embodiments.

FIG. 6 illustrates the basic structure of a CT scanner apparatus that includes the detectors described herein. The CT apparatus of FIG. 6 includes an X-ray tube 1, filters and collimators 2, and detector 3. As shown in FIG. 1, the CT apparatus also includes sparse, fixed energy-discriminating detectors, creating a $4^{th}$-generation scanner. The CT apparatus will also include additional mechanical and electrical components such as a gantry motor and a controller 4 to control the rotation of the gantry, control the X-ray source, and control a patient bed. The CT apparatus also includes a data acquisition system 5 and a processor 6 to generate CT images based on the projection (view) data acquired by the data acquisition system. The processor can be a CPU or other hardware processing circuit that can execute a computer program. The processor and data acquisition system make use of a memory 7, which is configured to store, e.g., projection data obtained from the detector and reconstructed images.

In one embodiment, the processor includes a reconstruction processor configured to reconstruct a series of offset CT images based on collected projection data, as discussed above. The processor is also configured/programmed to perform the steps set forth in the flowcharts of FIGS. 2A and 2B.

In one embodiment, the $4^{th}$-generation spectral computed tomography (CT) scanner apparatus shown in FIGS. 1 and 6 includes a rotating X-ray source 1, a $3^{rd}$-generation detector 3, and a plurality of fixed, energy-discriminating detectors (FIG. 1). Further, the hardware processor (processing circuit) 6 is configured to execute a program that causes the processing circuit to (1) obtain, from a hardware memory, a plurality of offset images, each offset image being obtained from a scan executed with the ring of fixed energy-discriminating detectors positioned in a known offset location with respect to the iso-center of the third-generation X-ray source/detector system; (2) cause the controller to perform a current scan executed with the ring of fixed energy-discriminating detectors positioned in an unknown offset location with respect to the iso-center of the third-generation X-ray source/detector system, to obtain a current image; (3) calculate, for each offset image, a corresponding error value between the offset image and the current image to obtain a plurality of error values; (4) determine a smallest error value of the plurality of error values; and (5) determine the positional offset of the center of the ring of fixed energy-discriminating detectors to be an offset location corresponding to an offset image, of the plurality of offset images, having the determined smallest error value.

As one of ordinary skill in the art would recognize, the processor 6 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art.

Once processed by the pre-reconstruction processor, the processed signals are passed to the reconstruction processor, which is configured to generate CT images. The images are stored in the memory, and/or displayed on a display. As one of ordinary skill in the art would recognize, memory can be a hard disk drive, CD-ROM drive, DVD drive, FLASH drive, RAM, ROM or any other electronic storage known in the art. The display can be implemented as an LCD display, CRT display, plasma display, OLED, LED or any other display known in the art. As such, the descriptions of the memory and the display provided herein are merely exemplary and in no way limit the scope of the present advancements.

While certain embodiments have been described, these embodiments have been presented by way of example only, and are not intended to limit the scope of the inventions. Indeed the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A method for determining, for a fourth-generation computed tomography (CT) scanner, a positional offset of a center of a ring of fixed energy-discriminating detectors with respect to an iso-center of a third-generation X-ray source/detector system, the method comprising:
   obtaining a plurality of offset images, each offset image being obtained from a scan executed with the ring of fixed energy-discriminating detectors positioned in a known offset location with respect to the iso-center of the third-generation X-ray source/detector system;
   performing a current scan executed with the ring of fixed energy-discriminating detectors positioned in an unknown offset location with respect to the iso-center of the third-generation X-ray source/detector system, to obtain a current image;
   calculating, for each offset image, a corresponding error value between the offset image and the current image to obtain a plurality of error values;
   determining a smallest error value of the plurality of error values; and
   determining the positional offset of the center of the ring of fixed energy-discriminating detectors to be an offset location corresponding to an offset image, of the plurality of offset images, having the determined smallest error value.

2. The method of claim 1, wherein the obtaining step comprises obtaining the offset images from a database of offset images, each offset image being generated by an air scan or a scan of a known phantom.

3. The method of claim 1, wherein the calculating step comprises:
   calculating, for each offset image, a mean-squared error between pixels in the current image and pixels in the offset image.

4. The method of claim 1, wherein the obtaining step comprises obtaining the plurality of offset images so that the plurality of offset images include images generated when the ring of fixed energy-discriminating detectors is positioned at various known offset positions around the iso-center of the third-generation X-ray source/detector system.

5. The method of claim 1, wherein the known offset positions are arranged in a two-dimensional grid centered at the iso-center of the third-generation X-ray source/detector system.

6. A method for determining, for a fourth-generation computed tomography (CT) scanner, a positional offset of a center of a ring of fixed energy-discriminating detectors with respect to an iso-center of a third-generation X-ray source/detector system, the method comprising:
   obtaining a plurality of offset images, each offset image being obtained from a scan executed with the ring of fixed energy-discriminating detectors positioned in a known offset location with respect to the iso-center of the third-generation X-ray source/detector system;
   performing a current scan executed with the ring of fixed energy-discriminating detectors positioned in an unknown offset location with respect to the iso-center of the third-generation X-ray source/detector system, to obtain a current image;
   calculating, for each offset image, a corresponding correlation value between the offset image and the current image to obtain a plurality of error values;
   determining a largest correlation value of the plurality of correlation values; and
   determining the positional offset of the center of the ring of fixed energy-discriminating detectors to be an offset location corresponding to an offset image, of the plurality of offset images, having the determined largest correlation value.

7. The method of claim 6, wherein the obtaining step comprises obtaining the offset images from a database of offset images, each offset image being generated by an air scan or a scan of a known phantom.

8. The method of claim 6, wherein the obtaining step comprises obtaining the plurality of offset images so that the plurality of offset images include images generated when the ring of fixed energy-discriminating detectors is positioned at various known offset positions around the iso-center of the third-generation X-ray source/detector system.

9. The method of claim 6, wherein the known offset positions are arranged in a two-dimensional grid centered at the iso-center of the third-generation X-ray source/detector system.

10. An apparatus for determining, in a fourth-generation computed tomography (CT) scanner, a positional offset of a center of a ring of fixed energy-discriminating detectors with respect to an iso-center of a third-generation X-ray source/detector system, the apparatus comprising:
 a processing circuit configured to execute a program that causes the processing circuit to
 obtain a plurality of offset images, each offset image being obtained from a scan executed with the ring of fixed energy-discriminating detectors positioned in a known offset location with respect to the iso-center of the third-generation X-ray source/detector system;
 perform a current scan executed with the ring of fixed energy-discriminating detectors positioned in an unknown offset location with respect to the iso-center of the third-generation X-ray source/detector system, to obtain a current image;
 calculate, for each offset image, a corresponding error value between the offset image and the current image to obtain a plurality of error values;
 determine a smallest error value of the plurality of error values; and
 determine the positional offset of the center of the ring of fixed energy-discriminating detectors to be an offset location corresponding to an offset image, of the plurality of offset images, having the determined smallest error value.

11. The apparatus of claim 10, further comprising:
 a memory that stores the plurality of offset images, each offset image being stored in association with a corresponding offset location of the offset image.

12. An apparatus for determining, for a fourth-generation computed tomography (CT) scanner, a positional offset of a center of a ring of fixed energy-discriminating detectors with respect to an iso-center of a third-generation X-ray source/detector system, the apparatus comprising:
 a processing circuit configured to execute a program that causes the processing circuit to
 obtain a plurality of offset images, each offset image being obtained from a scan executed with the ring of fixed energy-discriminating detectors positioned in a known offset location with respect to the iso-center of the third-generation X-ray source/detector system;
 perform a current scan executed with the ring of fixed energy-discriminating detectors positioned in an unknown offset location with respect to the iso-center of the third-generation X-ray source/detector system, to obtain a current image;
 calculate, for each offset image, a corresponding correlation value between the offset image and the current image to obtain a plurality of error values;
 determine a largest correlation value of the plurality of correlation values; and
 determine the positional offset of the center of the ring of fixed energy-discriminating detectors to be an offset location corresponding to an offset image, of the plurality of offset images, having the determined largest correlation value.

13. The apparatus of claim 12, further comprising:
 a memory that stores the plurality of offset images, each offset image being stored in association with a corresponding offset location of the offset image.

* * * * *